(12) United States Patent
Von Berg et al.

(10) Patent No.: US 12,400,357 B2
(45) Date of Patent: Aug. 26, 2025

(54) APPARATUS FOR DETERMINING AN ORIENTATION OF A PATIENT'S CHEST

(71) Applicant: KONINKLIJKE PHILIPS N.V., Eindhoven (NL)

(72) Inventors: Jens Von Berg, Hamburg (DE); Sven Krönke, Hamburg (DE); Daniel Bystrov, Hamburg (DE); Stewart Matthew Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 474 days.

(21) Appl. No.: 17/772,287

(22) PCT Filed: Oct. 29, 2020

(86) PCT No.: PCT/EP2020/080460
§ 371 (c)(1),
(2) Date: Apr. 27, 2022

(87) PCT Pub. No.: WO2021/084041
PCT Pub. Date: May 6, 2021

(65) Prior Publication Data
US 2022/0375120 A1 Nov. 24, 2022

(30) Foreign Application Priority Data
Oct. 31, 2019 (EP) .................... 19206544

(51) Int. Cl.
*A61B 6/04* (2006.01)
*A61B 6/50* (2024.01)
*G06T 7/73* (2017.01)

(52) U.S. Cl.
CPC ............... *G06T 7/73* (2017.01); *A61B 6/505* (2013.01); *G06T 2207/10116* (2013.01); *G06T 2207/30004* (2013.01)

(58) Field of Classification Search
None
See application file for complete search history.

(56) References Cited

U.S. PATENT DOCUMENTS

| 5,668,888 A | 9/1997 | Doi |
| 8,900,146 B2 | 12/2014 | Zheng |

(Continued)

FOREIGN PATENT DOCUMENTS

| KR | 20170062789 A | 6/2017 |
| RU | 2454179 C1 | 6/2012 |

OTHER PUBLICATIONS

IPCOM000174149D, Method and apparatus to automatically determine patient orientation for X-ray chest examination. Ip.com Prior Art Database Technical Disclosure. Aug. 28, 2008. (Year: 2008).*

(Continued)

*Primary Examiner* — Amandeep Saini
*Assistant Examiner* — Caroline Tabancay Duffy
(74) *Attorney, Agent, or Firm* — Larry Liberchuk

(57) ABSTRACT

An orientation of a patient's chest is determined by an apparatus and method. According to the invention, a camera image of a patient comprising image data of the patient's chest is received, wherein the camera image is acquired with an optical camera. Further, an X-ray radiograph of the patient's chest with an X-ray imaging axis extending from an X-ray source to an X-ray detector is received. Then, the camera image and the X-ray radiograph are provided to at least one processor. Further, information relating to a clavicle to spinous process distance of the patient is then determined using the camera image. Finally, an orientation of the patient's chest in the X-ray radiograph with respect to the X-ray imaging axis is determined using the camera image, the X-ray radiograph, and the information relating to the clavicle to spinal process distance of the patient.

11 Claims, 3 Drawing Sheets

(56) References Cited

U.S. PATENT DOCUMENTS

| | | | |
|---|---|---|---|
| 9,466,106 B2 | 10/2016 | Kobayashi | |
| 10,820,835 B2 | 11/2020 | Gupta | |
| 2007/0171225 A1* | 7/2007 | Haex | G06T 7/0012 |
| | | | 345/473 |
| 2015/0313566 A1* | 11/2015 | Diers | A61B 6/505 |
| | | | 378/63 |
| 2017/0224302 A1 | 8/2017 | Von Berg | |
| 2019/0378329 A1* | 12/2019 | Kiely | A61B 5/349 |
| 2020/0008676 A1* | 1/2020 | Dong | A61B 5/0035 |
| 2024/0023809 A1* | 1/2024 | DeBaun | A61B 5/4576 |

OTHER PUBLICATIONS

IPCOM000245139D, Technique for Dynamic Assessment of Patient Position and Motion in Digital Radiography Exams. Ip.com Prior Art Database Technical Disclosure. Feb. 12, 2016. (Year: 2016).*

Dewi, D. E. O. et al. (2010). Reproducibility of Standing Posture for X-Ray Radiography: A Feasibility Study of the BalancAid with Healthy Young Subjects. Annals of Biomedical Engineering, 38(10), 3237-3245. https://doi.org/10.1007/s10439-010-0062-y (Year: 2010).*

Hardy M, Scotland B, Herron L. Assessing Sagittal Rotation on Posteroanterior Chest Radiographs: The Effect of Body Morphology on Radiographic Appearances. J Med Imaging Radiat Sci. Dec. 2015;46(4):365-371. doi: 10.1016/j.jmir.2015.07.004. PMID: 31052116. (Year: 2015).*

Von Berg J, Krönke S, Gooßen A, Bystrov D, Brück M, Harder T, Wieberneit N, Young S, "Robust chest x-ray quality assessment using convultional neural networks and atlas regularization," Proc. SPIE 11313, Medical Imaging 2020: Image Processing, 113131L. (Year: 2020).*

PCT International Search Report, International application No. PCT/EP2020/080460, Jan. 14, 2021.

Hardy M. et al., "Assessing Sagittal Rotation on Posteroanterior Chest Radiographs: The Effect of Body Morphology on Radiographic Appearances", Journal of Medical Imaging and Radiation Sciences, Elsevi Er, Amsterdam, NL, vol. 46, No. 4, Dec. 8, 2015, pp. 365-371, XP029338984.

Von Berg J. et al., "Temporal Subtraction of Chest Radiographs Compensating Pose Differences", Proc. of SPIE 2011, Dec. 31, 2011 (Dec. 31, 2011), XP040557381.

Naveed A. et al., "X-Ray Patient Positioning Manual", Internet Citation, Dec. 21, 2001 (Dec. 21, 2001), pp. 126-152, XP002738359, Retrieved from the Internet: http://cdn.auntminnie.com/user/documents/content documents/X-RayPatientPositioningManual 080402.pdf— [retrieved on Apr. 13, 2015] p. 8-11.

Santosh K.C. et al., "Automatically Detecting Rotation in Chest Radiographs Using Principal Rib-Orientation Measure for Quality Control", International Journal of Pattern Recognition and Artificial Intelligence, vol. 29, No. 2, 2014.

* cited by examiner

APPARATUS FOR DETERMINING AN ORIENTATION OF A PATIENT'S CHEST

FIELD OF THE INVENTION

The present invention relates to an apparatus for determining an orientation of a patient's chest, an X-ray imaging system, a method for determining an orientation of a patient's chest, as well as to a computer program element and a computer readable medium.

BACKGROUND OF THE INVENTION

International guidelines require that the orientation (or rotational position about a longitudinal axis) of a patient during a chest posterior-anterior (PA) or anterior-posterior (AP) x-ray acquisition be determined by measuring the projections of some anterior (clavicle heads) and posterior (spinous processes) landmarks in the image for quality checks. For example, international guidelines instruct to check whether the spinal processes of the vertebrae are positioned in the centre between the two clavicle heads. This is in order to determine if the patient's chest is orientated directly toward the X-ray source along a source to detector axis, or is twisted to a greater or lesser degree. In order to quantify the rotation angle from this underdetermined setting, it is assumed that the distances between these landmarks measured in the actual 3D body correlate with each other, i.e. that a large patient is just an isotropically scaled small patient. Thus, it is intended that a rotation angle can be estimated from the location of the three anatomical landmarks left clavicle head ($C_1$), right clavicle head $C_r$ and spinal process (p), and this angle can be used to determine if a given threshold angle, either to the left or to the right, has been exceeded requiring a re-scan. Unfortunately, the distances between these three landmarks cannot easily be determined from the PA chest radiograph, especially the distances P to $C_1$ and distances P to $C_r$ cannot be estimated well as these lines are almost parallel to the x-rays. It has been proposed that anatomical a priori estimates be used, assuming that the patient does not vary too much from an average anatomy. The whole method is proposed to be scale invariant and would then work with small people as well as with large people as long as the ratio ρ between P to $C_1$ and $C_r$ to $C_1$ can be taken as constant across the population. Unfortunately again, studies have shown that in a set of patients both distances P to $C_1$ and $C_r$ to $C_1$ do not correlate with each other [see Hardy, Scotland, Herron. "Assessing Sagittal Rotation on Posteroanterior Chest Radiographs: The Effect of Body Morphology on Radiographic Appearances" Journal of Medical Imaging and Radiation Sciences 46 (2015)]. Following that study, it is clear that the difference in body shape to be observed in a population counteracts precise estimation of the rotation angle from the projected landmarks in a PA chest radiograph. For example, for some distances measured, the angle may vary between 5 deg and 10 deg of rotation according to the individual ratio ρ as observed in the sample. This range would make the applicability of an angular threshold value difficult or quite imprecise. In other words, empirical evidence from Computer Tomography (CT) samples has shown, that the interclavicle distance does not correlate with the clavicle to spinal process distance in real patients.

It is important to determine the orientation of the patient's chest, in order to assess the quality of a chest radiograph, because rotation of the chest away from an alignment with the source to detector axis can compromise image quality for different reasons. In rotated patients, more lung parenchyma is shadowed by the mediastinum and the lung-heart-ratio is faulty, and generally these rotated images can both mimic and mask all kinds of diseases. Positioning a patient straight with respect to the source to detector axis is therefore important for the diagnostic quality, and if the patient is rotated it is required to determine by how much in order that a determination can be made if a re-scan is necessary. However, as discussed above there is no way of accurately determining this orientation of rotation angle across the population.

There is a need to address these issues.

SUMMARY OF THE INVENTION

It would be advantageous to have improved means of determining an orientation of a patient undergoing an X-ray radiograph examination.

The object of the present invention is solved with the subject matter of the independent claims, wherein further embodiments are incorporated in the dependent claims. It should be noted that the following described aspects and examples of the invention apply also to the apparatus for determining an orientation of a patient's chest, the X-ray imaging system, the method for determining an orientation of a patient's chest, as well as to the computer program element and a computer readable medium.

In a first aspect, there is provided an apparatus for determining an orientation of a patient's chest, the apparatus comprising:

an input unit; and
a processing unit.

The input unit is configured to receive an image of a patient, the image comprising image data of the patient's chest. The input unit is configured to receive an X-ray radiograph of the patient's chest acquired by an X-ray imaging unit with an X-ray imaging axis extending from an X-ray source to an X-ray detector. The input unit is configured to provide the image and the X-ray radiograph to the processing unit. The processing unit is configured to determine an orientation of the patient's chest in the X-ray radiograph with respect to the X-ray imaging axis, the determination comprising utilization of the image and the X-ray radiograph.

In this manner, for example for an AP or PA X-ray radiograph of the patient's chest the quality of a chest radiograph can be assessed by determining if the patient was correctly aligned or whether he or she was rotated about their longitudinal direction with respect to the imaging axis of the X-ray imaging unit that acquired the X-ray radiograph. By determining the orientation of the patient, in terms of whether they are rotated or not, enables it to be determined if the image would impede analysis or not. For example, in rotated patients more lung parenchyma is shadowed by the mediastinum and the lung-heart-ratio is faulty, and it can be determined if the X-ray radiograph acquired is appropriate for a correct analysis, or whether a repeat scan is required. Thus, such rotated images may both mimic and mask all kinds of diseases, and the apparatus enables a determination to be made if the patient was positioned "straight" or whether they were rotated, thereby providing an important diagnostic for image quality.

Furthermore, the apparatus facilitates the meeting of international guidelines that instruct that a check be made whether the spinal processes of the vertebrae are positioned in the centre between the two clavicle heads for an AP or PA X-ray radiograph, and indeed to determine an angle of rotation away from this ideal.

In an example, the processing unit is configured to determine information relating to a clavicle to spinous process distance of the patient, the determination comprising utilization of the image. Determination of the orientation of the patient's chest in the X-ray radiograph with respect to the X-ray imaging axis comprises utilization of the information relating to the clavicle to spinal process distance of the patient.

In other words, the clavicle to spinous process distance can be estimated from an image, such as acquired by a camera or acquired by the X-ray imaging unit itself as a lateral chest X-ray radiograph that is typically taken along with a PA or AP chest X-ray radiograph. Thus, this information of the patient is used in order to obtain a more precise estimation of the patient's rotation about their longitudinal with respect to the X-ray source to X-ray detector imaging axis.

In an example, the information relating to the clavicle to spinous process distance of the patient comprises a determined clavicle to spinal process distance of the patient.

In an example, the processing unit is configured to determine information relating to one or more of: a left clavicle head; a right clavicle head; a spinal process of the patient, the determination comprising utilization of the X-ray radiograph. Determination of the orientation of the patient's chest in the X-ray radiograph with respect to the X-ray imaging axis comprises utilization of the information relating to one or more of: the left clavicle head; the right clavicle head; the spinal process of the patient.

In an example, the information relating to one or more of: the left clavicle head; the right clavicle head; the spinal process of the patient comprises locations in the X-ray radiograph of one or more of the left clavicle head; the right clavicle head; the spinal process of the patient.

In an example, the information relating to one or more of: the left clavicle head; the right clavicle head; the spinal process of the patient comprises relative location information in the X-ray radiograph of two or more of the left clavicle head; the right clavicle head; the spinal process of the patient.

In an example, the information relating to one or more of: the left clavicle head; the right clavicle head; the spinal process of the patient comprises a distance in the X-ray radiograph between the left clavicle head and the right clavicle head.

In an example, the information relating to one or more of: the left clavicle head; the right clavicle head; the spinal process of the patient comprises a distance in the X-ray radiograph between the left clavicle head and the spinous process.

In an example, the information relating to one or more of: the left clavicle head; the right clavicle head; the spinal process of the patient comprises a distance in the X-ray radiograph between the right clavicle head and the spinous process.

In an example, the information relating to one or more of: the left clavicle head; the right clavicle head; the spinal process of the patient comprises locations of the left clavicle head, the right clavicle head, and the spinal process in the X-ray radiograph relative to each other.

In an example, the information relating to one or more of: the left clavicle head; the right clavicle head; the spinal process of the patient comprises distances between the left clavicle head, the right clavicle head, and the spinal process in the X-ray radiograph with respect to each other.

In an example, the orientation of the patient's chest about a longitudinal axis of the patient is determined.

In this manner, an image of the patient can be used to determine the clavicle to spinal process distance for the patient, and then the relative positions of the left clavicle head to the right clavicle head and the spinal process of the patient in the X-ray radiograph in effect enables a 3D relative positioning of these three features to be determined, from which the orientation, in terms of rotation of the patient's chest about their longitudinal axis with respect to the X-ray imaging axis can be determined.

In a second aspect, there is provided an X-ray imaging system, the system comprising:
an X-ray imaging unit; and
an apparatus (10) for determining an orientation of a patient's chest (PC) according to the first aspect.

The X-ray imaging unit comprises an X-ray source and an X-ray detector with an X-ray imaging axis extending from the X-ray source to the X-ray detector. The X-ray imaging unit is configured to acquire an X-ray radiograph of the patient's chest. The apparatus is configured to determine an orientation of the patient's chest in the X-ray radiograph with respect to the X-ray imaging axis. The determination comprises utilization of the X-ray radiograph and an image of the patient other than the X-ray radiograph that comprises image data of the patient's chest.

In a third aspect, there is provided a method for determining an orientation of a patient's chest, the method comprising:
a) receiving an image of a patient, the image comprising image data of the patient's chest;
b) receiving an X-ray radiograph of the patient's chest acquired by an X-ray imaging unit with an X-ray imaging axis extending from an X-ray source to an X-ray detector;
c) providing the image and the X-ray radiograph to a processing unit; and
f) determining by the processing unit an orientation of the patient's chest in the X-ray radiograph with respect to the X-ray imaging axis, the determination comprising utilization of the image and the X-ray radiograph.

According to another aspect, there is provided a computer program element for controlling one or more of the apparatuses and/or systems as previously described which, if the computer program element is executed by a processing unit, is adapted to perform one or more of the methods as previously described.

According to another aspect, there is provided a computer readable medium having stored the computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
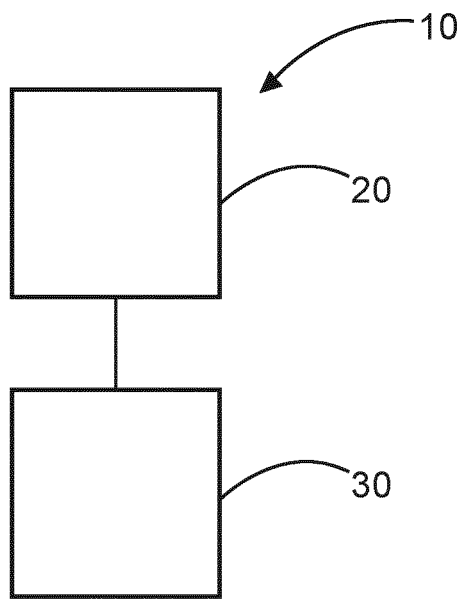
FIG. 1 shows a schematic set up of an example of an apparatus for determining an orientation of a patient's chest.

FIG. 1 shows an example of an apparatus 10 for determining an orientation of a patient's chest. The apparatus comprises an input unit 20, and a processing unit 30. The input unit is configured to receive an image of a patient, the image comprising image data of the patient's chest. The input unit is configured also to receive an X-ray radiograph of the patient's chest acquired by an X-ray imaging unit with an X-ray imaging axis extending from an X-ray source to an X-ray detector. The input unit is configured also to provide the image and the X-ray radiograph to the processing unit. The processing unit is configured to determine an orientation of the patient's chest in the X-ray radiograph with respect to the X-ray imaging axis. The determination comprises utilization of the image and the X-ray radiograph.

In an example, the orientation comprises an angle of rotation.

In an example, the orientation comprises an angle of rotation away from an ideal AP or PA acquisition orientation.

In an example, the image of the patient is an optical image.

In an example, the image of the patient is an optical image acquired by an optical depth camera.

In an example, the image of the patient is an x-ray image.

In an example, the image of the patient is acquired by the X-ray imaging unit.

In an example, the image of the patient is acquired by the X-ray imaging unit, where the image is of a view of the patient that is substantially perpendicular to the view of the patient for the X-ray radiograph. Thus, for example if the X-ray radiograph is intended to be a PA or a AP radiograph of the patient's chest, then the image is of a lateral view of the patient's chest.

In an example the image of the patient is a lateral image of the patient.

According to an example, the processing unit is configured to determine information relating to a clavicle to spinous process distance of the patient, the determination comprising utilization of the image. Determination of the orientation of the patient's chest in the X-ray radiograph with respect to the X-ray imaging axis comprises utilization of the information relating to the clavicle to spinal process distance of the patient.

According to an example, the information relating to the clavicle to spinous process distance of the patient comprises a determined clavicle to spinal process distance of the patient.

In an example, the determined clavicle to spinous process distance of the patient comprises a distance between one or both clavicle heads and the spinous process. In an example, the determined clavicle to spinous process distance of the patient comprises an average distance both clavicle heads and the spinous process.

According to an example, the processing unit is configured to determine information relating to one or more of: a left clavicle head 50; a right clavicle head 60; a spinal process of the patient 70, the determination comprising utilization of the X-ray radiograph. Determination of the orientation of the patient's chest in the X-ray radiograph with respect to the X-ray imaging axis comprises utilization of the information relating to one or more of: the left clavicle head; the right clavicle head; the spinal process of the patient.

According to an example, the information relating to one or more of: the left clavicle head; the right clavicle head; the spinal process of the patient comprises locations in the X-ray radiograph of one or more of the left clavicle head; the right clavicle head; the spinal process of the patient.

According to an example, the information relating to one or more of: the left clavicle head; the right clavicle head; the spinal process of the patient comprises relative location information in the X-ray radiograph of two or more of the left clavicle head; the right clavicle head; the spinal process of the patient.

According to an example, the information relating to one or more of: the left clavicle head; the right clavicle head; the spinal process of the patient comprises a distance in the X-ray radiograph between the left clavicle head and the right clavicle head.

According to an example, the information relating to one or more of: the left clavicle head; the right clavicle head; the spinal process of the patient comprises a distance in the X-ray radiograph between the left clavicle head and the spinous process.

According to an example, the information relating to one or more of: the left clavicle head; the right clavicle head; the spinal process of the patient comprises a distance in the X-ray radiograph between the right clavicle head and the spinous process.

According to an example, the information relating to one or more of: the left clavicle head; the right clavicle head; the spinal process of the patient comprises locations of the left clavicle head, the right clavicle head, and the spinal process in the X-ray radiograph relative to each other.

According to an example, the information relating to one or more of: the left clavicle head; the right clavicle head; the spinal process of the patient comprises distances between the left clavicle head, the right clavicle head, and the spinal process in the X-ray radiograph with respect to each other.

According to an example, the orientation of the patient's chest about a longitudinal axis of the patient is determined. In an example, the longitudinal axis of the patient is substantially perpendicular to the X-ray imaging axis.

Figure 2:
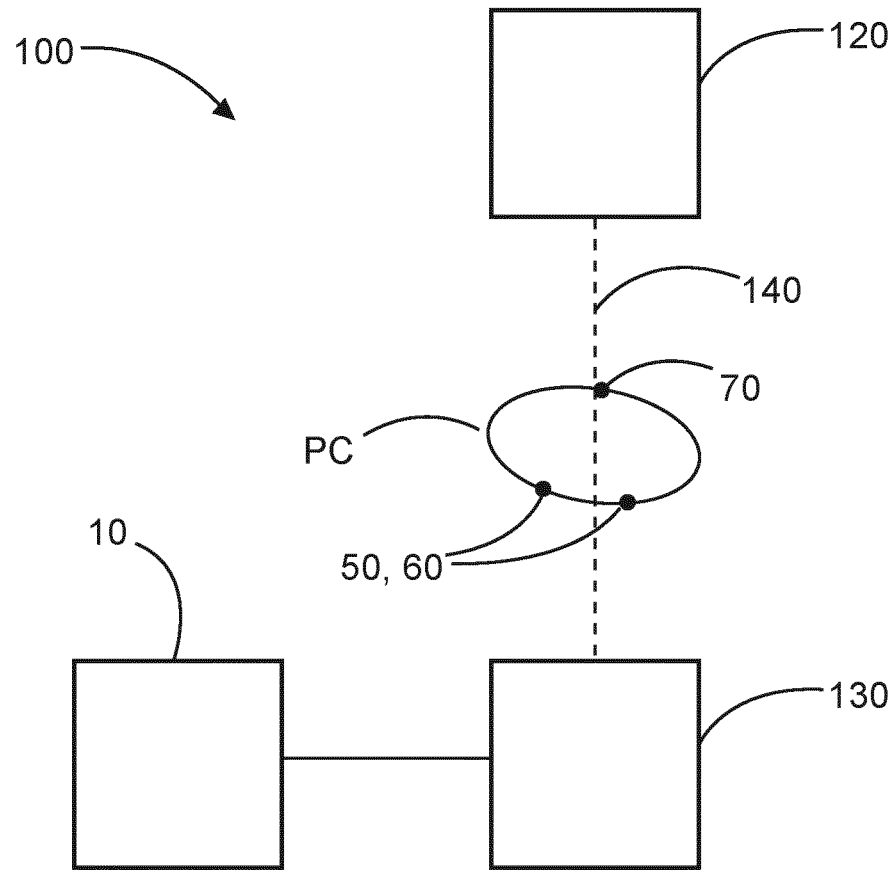
FIG. 2 shows a schematic set up of an example of an X-ray imaging system.

FIG. 2 shows an example of an X-ray imaging system 100. The system 100 comprises an X-ray imaging unit 110, and an apparatus 10 for determining an orientation of a patient's chest (PC) as described with respect to FIG. 1. The X-ray imaging unit comprises an X-ray source 120 and an X-ray detector 130 with an X-ray imaging axis 140 extending from the X-ray source to the X-ray detector. The X-ray imaging unit is configured to acquire an X-ray radiograph of the patient's chest, such as a. The apparatus is configured to determine an orientation of the patient's chest in the X-ray radiograph with respect to the X-ray imaging axis. The determination comprising utilization of the X-ray radiograph and an image of the patient that comprises image data of the patient's chest, where this image is other than (in other words different to) the X-ray radiograph of the patient's.

Figure 3:
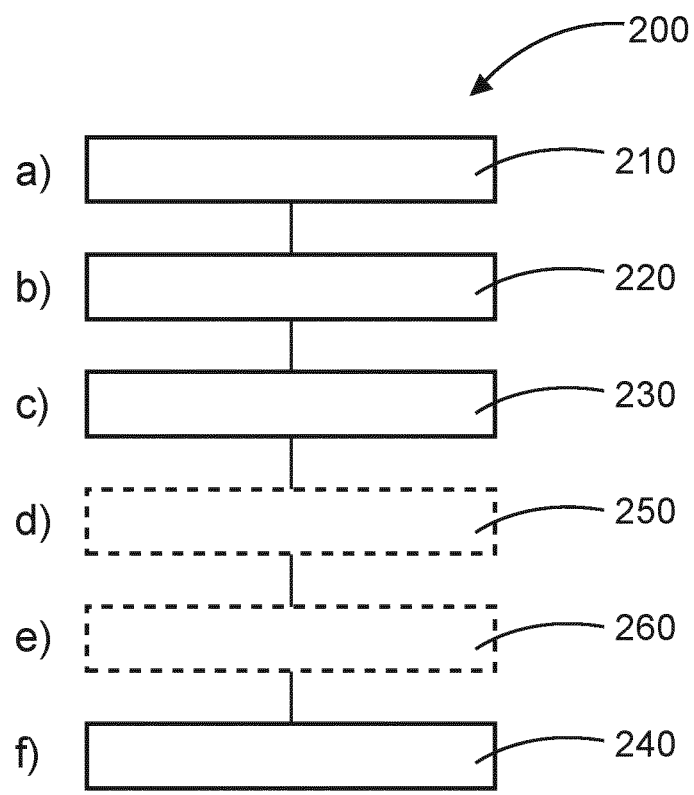
FIG. 3 shows a method for determining an orientation of a patient's chest.

FIG. 3 shows a method 200 for determining an orientation of a patient's chest in its basic steps, where essential steps are shown in solid lines and optional steps are shown in dashed lines. The method 200 comprises:

in a receiving step 210, also referred to as step a), receiving an image of a patient, the image comprising image data of the patient's chest;

in a receiving step 220, also referred to as step b), receiving an X-ray radiograph of the patient's chest acquired by an X-ray imaging unit with an X-ray imaging axis extending from an X-ray source to an X-ray detector;

in a providing step 230, also referred to as step c), providing the image and the X-ray radiograph to a processing unit; and in a determining step 240, also referred to as step f), determining by the processing unit an orientation of the patient's chest in the X-ray radiograph with respect to the X-ray imaging axis, the determination comprising utilization of the image and the X-ray radiograph.

In an example, the method comprises step d) determining 250 by the processing unit information relating to a clavicle to spinous process distance of the patient, the determining comprising utilizing the image, and wherein step f) comprises utilizing the information relating to the clavicle to spinous process distance of the patient.

In an example, in step d) determining the information relating to the clavicle to spinous process distance of the patient comprises determining a clavicle to spinous process distance of the patient.

In an example, the method comprises step e) determining 260 by the processing unit information relating to one or more of: a left clavicle head; a right clavicle head; a spinal process of the patient, the determining comprising utilizing the X-ray radiograph, and wherein step f) comprises utilizing the information relating to one or more of: the left clavicle head; the right clavicle head; the spinal process of the patient.

In an example, in step e) determining the information relating to one or more of: the left clavicle head; the right clavicle head; the spinal process of the patient comprises determining locations in the X-ray radiograph of one or more of the left clavicle head; the right clavicle head; the spinal process of the patient.

In an example, in step e) determining the information relating to one or more of: the left clavicle head; the right clavicle head; the spinal process of the patient comprises determining relative location information in the X-ray radiograph of two or more of the left clavicle head; the right clavicle head; the spinal process of the patient.

In an example, in step e) determining the information relating to one or more of: the left clavicle head; the right clavicle head; the spinal process of the patient comprises determining a distance in the X-ray radiograph between the left clavicle head and the right clavicle head.

In an example, in step e) determining the information relating to one or more of: the left clavicle head; the right clavicle head; the spinal process of the patient comprises determining a distance in the X-ray radiograph between the left clavicle head and the spinous process.

In an example, in step e) determining the information relating to one or more of: the left clavicle head; the right clavicle head; the spinal process of the patient comprises determining a distance in the X-ray radiograph between the right clavicle head and the spinous process.

In an example, in step e) determining the information relating to one or more of: the left clavicle head; the right clavicle head; the spinal process of the patient comprises determining locations of the left clavicle head, the right clavicle head, and the spinal process in the X-ray radiograph relative to each other.

In an example, in step e) determining the information relating to one or more of: the left clavicle head; the right clavicle head; the spinal process of the patient comprises determining distances between the left clavicle head, the right clavicle head, and the spinal process in the X-ray radiograph with respect to each other.

In an example, in step f) the orientation of the patient's chest is determined about a longitudinal axis of the patient.

The apparatus for determining an orientation of a patient's chest, the X-ray imaging system, and the method for determining an orientation of a patient's chest will now be discussed in specific detail, where reference is made to FIGS. 4-6.

Figure 4:
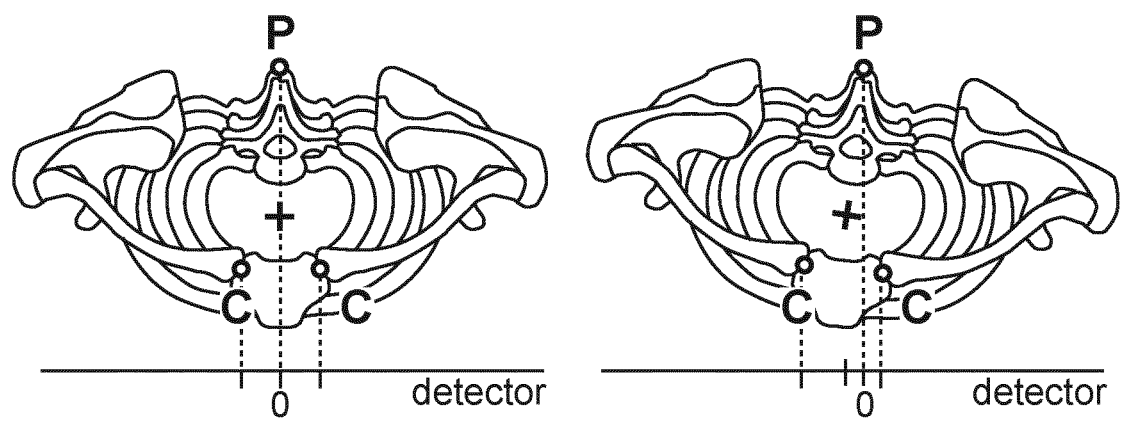
FIG. 4 shows projection geometry in a plane cut through patient in front of an x-ray detector with the x-ray source is positioned parallel to the x-ray detector, showing the locations of the spinal process (p), left clavicle head ($C_l$), right clavicle head ($C_r$)
Figure 5:
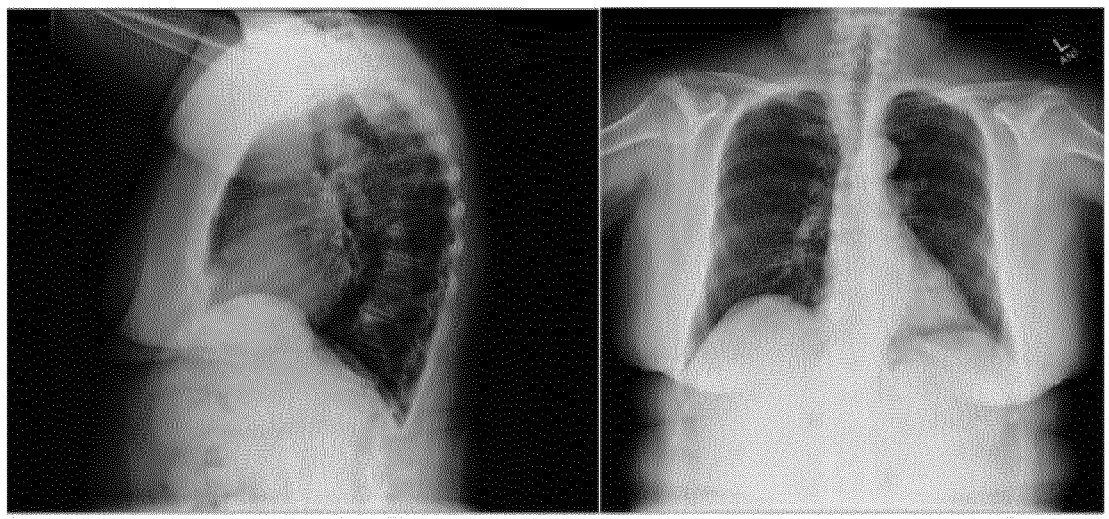
FIG. 5 shows lateral and PA radiographs of the same patient.

FIG. 4 shows the three anatomical landmarks left clavicle head ($C_l$), right clavicle head ($C_r$) and spinal process (p), and shows the projections of these landmark features on the detector for both a patient is correctly aligned along the source to detector axis, and for a patient who is slightly rotated. As seen at the detector plane, the projections of these features acquired at the detector move relative to each other as the patient rotates. As discussed above, existing methods to determine this rotation angle based on an assumed spinal process to clavicle head distance for different patients does not work, due to variability across the population. The inventors realised that information on the spinal process to clavicle head distance could be determined from an image different to the PA or AP x-ray radiograph acquired. In an x-ray scan process where a PA or AP x-ray radiograph was acquired, a lateral chest radiograph is also typically acquired. Such a lateral radiograph and PA radiograph for the same patient are shown in FIG. 5. Therefore, the inventors realised that this lateral radiograph, or indeed an image acquired by a camera that could be a 3-D camera, can be used to estimate or determine the spinal process to clavicle head distance.

Figure 6:
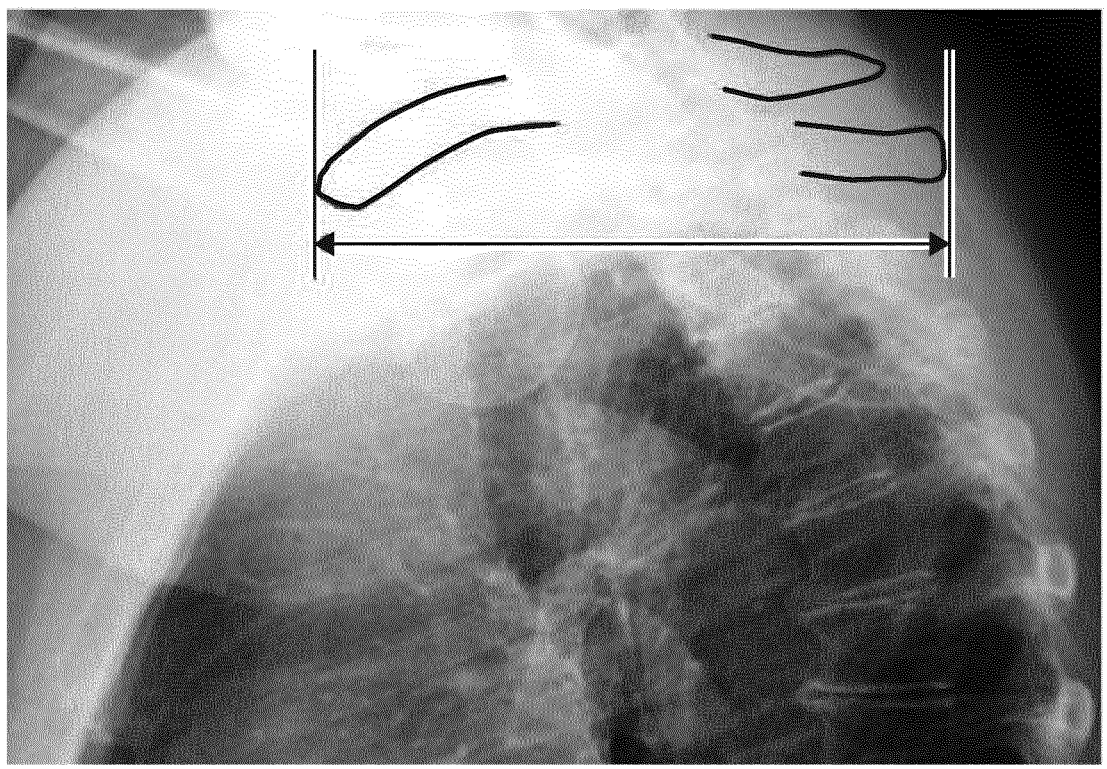
FIG. 6 shows a lateral radiograph, with the left clavicle and spinous process indicated.

As shown in FIG. 6, the spinal process left or right clavicle head can be located in the lateral chest radiograph, enabling the spinal process to clavicle head distance to be determined. Then as indicated in FIG. 4 the projected distances of the three landmarks on the PA (or AP) chest radiograph are measured. The interclavicle distance ($C_r$ to $C_l$) is taken from the PA (or AP) while as discussed above the clavicle to spinous distance (P to $C_l$) is taken from the lateral radiograph. Having these distance estimates from patient measures allows for a more precise estimate of the rotation angle which is the pre requisite for working with a quantitative angular threshold in order to consistently reject images for rotation issues. This rotation angle estimation, once the spinal process to clavicle distances known, can be determined through a econometric relationships as would be appreciated by the skilled person when looking at FIG. 4 because the projections of the left and right clavicle head and the spinal process can be measured with respect to one another in the PA (or AP) x-ray radiograph. Moreover, the measured clavicle to spinous distance may be electronically stored such that the rotation angle can be directly estimated from a PA image for any subsequent examination of the same patient.

As discussed above, the image other than the PA (or AP) radiograph need not be a lateral x-ray radiograph, but could be acquired by an optical camera such as a depth camera.

Here, information about the ratio ρ, discussed above, can be assessed from a depth camera image. Internal landmarks cannot directly be located, however the extent of the patient's upper chest can be measured both in lateral orientation and in PA orientation from a depth image. By correlating depth camera images to CT images of the same patient, one can statistically learn how to translate e.g. detected landmarks in the depth camera image to e.g. the P-$C_1$ distance. This relationship can then be used for estimating this distance from the depth camera image alone.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for determining an orientation of a patient's chest, comprising:
   at least one processor; and
   a memory containing instructions that, when executed by the at least one processor, configure the apparatus to:
   receive a camera image of a patient comprising image data of the patient's chest, wherein the camera image is acquired with an optical camera;
   receive an X-ray radiograph of the patient's chest with an X-ray imaging axis extending from an X-ray source to an X-ray detector;
   determine a clavicle to spinous process distance of the patient using the camera image; and
   in the X-ray radiograph, obtain an estimation of the patient's chest rotation about a longitudinal axis of the patient using the camera image, the X-ray radiograph, and the clavicle to spinous process distance of the patient.

2. The apparatus according to claim 1, wherein the at least one processor is configured to determine information relating to one or more of: a left clavicle head, a right clavicle head, and a spinous process of the patient, and wherein obtaining the estimation of the patient's chest rotation comprises using the information relating to one or more of: the left clavicle head, the right clavicle head, and the spinous process of the patient.

3. The apparatus according to claim 2, wherein the information relating to the left clavicle head, the right clavicle head, and the spinous process of the patient comprises locations in the X-ray radiograph of one or more of the left clavicle head, the right clavicle head, and the spinous process of the patient.

4. The apparatus according to claim 2, wherein the information relating to the left clavicle head, the right clavicle head, and the spinous process of the patient comprises relative location information in the X-ray radiograph of two or more of the left clavicle head, the right clavicle head, and the spinous process of the patient.

5. The apparatus according to claim 2, wherein the information relating to the left clavicle head, the right clavicle head, and the spinous process of the patient comprises a distance in the X-ray radiograph between the left clavicle head and the right clavicle head.

6. The apparatus according to claim 2, wherein the information relating to the left clavicle head, the right clavicle head, and the spinous process of the patient comprises a distance in the X-ray radiograph between the left clavicle head and the spinous process.

7. The apparatus according to claim 2, wherein the information relating to the left clavicle head, the right clavicle head, and the spinous process of the patient comprises a distance in the X-ray radiograph between the right clavicle head and the spinous process.

8. The apparatus according to claim 2, wherein the information relating to the left clavicle head, the right clavicle head, and the spinous process of the patient comprises locations of the left clavicle head, the right clavicle head, and the spinous process in the X-ray radiograph relative to each other.

9. The apparatus according to claim 2, wherein the information relating to the left clavicle head, the right clavicle head, and the spinous process of the patient comprises distances between the left clavicle head, the right clavicle head, and the spinous process in the X-ray radiograph with respect to each other.

10. A computer-implemented method for determining an orientation of a patient's chest, comprising:
    receiving a camera image of a patient comprising image data of the patient's chest, wherein the camera image is acquired with an optical camera;
    receiving an X-ray radiograph of the patient's chest with an X-ray imaging axis extending from an X-ray source to an X-ray detector;
    providing the camera image and the X-ray radiograph to at least one processor;
    determining a clavicle to spinous process distance of the patient using the camera image; and
    in the X-ray radiograph, obtaining, by the at least one processor, an estimation of the patient's chest rotation about a longitudinal axis of the patient using the camera image, the X-ray radiograph, and the clavicle to spinous process distance of the patient.

11. A non-transitory computer-readable medium for storing executable instructions, which cause a method to be performed for determining an orientation of a patient's chest, the method comprising:
    receiving a camera image of a patient comprising image data of the patient's chest, wherein the camera image is acquired with an optical camera;
    receiving an X-ray radiograph of the patient's chest with an X-ray imaging axis extending from an X-ray source to an X-ray detector;
    providing the camera image and the X-ray radiograph to at least one processor;
    determining a clavicle to spinous process distance of the patient using the camera image; and
    in the X-ray radiograph, obtaining, by the at least one processor, an estimation of the patient's chest rotation about a longitudinal axis of the patient using the camera image, the X-ray radiograph, and the clavicle to spinous process distance of the patient.

* * * * *